(12) United States Patent
Gazit et al.

(10) Patent No.: US 8,889,729 B2
(45) Date of Patent: Nov. 18, 2014

(54) COMPOSITIONS FOR TREATING AMYLOID ASSOCIATED DISEASES

(75) Inventors: Ehud Gazit, Ramat-HaSharon (IL); Tomer Cohen, Petach-Tikva (IL)

(73) Assignee: Tel Aviv University Future Technology Development L.P., Tel-Aviv (IL)

( * ) Notice: Subject to any disclaimer, the term of this patent is extended or adjusted under 35 U.S.C. 154(b) by 427 days.

(21) Appl. No.: 12/794,746

(22) Filed: Jun. 6, 2010

(65) Prior Publication Data
US 2010/0240726 A1 Sep. 23, 2010

Related U.S. Application Data

(63) Continuation of application No. 11/660,522, filed as application No. PCT/IL2005/000902 on Aug. 18, 2005, now Pat. No. 7,732,479.

(60) Provisional application No. 60/602,635, filed on Aug. 19, 2004, provisional application No. 60/649,574, filed on Feb. 4, 2005.

(51) Int. Cl.
*A61K 31/405* (2006.01)
*A61K 31/415* (2006.01)
*A61K 31/4164* (2006.01)
*A61K 31/403* (2006.01)
*C07D 209/12* (2006.01)
*A61K 31/404* (2006.01)
*C07D 209/32* (2006.01)

(52) U.S. Cl.
CPC ............ *C07D 209/12* (2013.01); *A61K 31/415* (2013.01); *A61K 31/4164* (2013.01); *A61K 31/403* (2013.01); *A61K 31/404* (2013.01); *C07D 209/32* (2013.01)

USPC ........... 514/415; 514/416; 514/418; 514/419; 514/493

(58) Field of Classification Search
USPC .......................... 514/415, 416, 418, 419, 493
See application file for complete search history.

(56) References Cited

U.S. PATENT DOCUMENTS

| | | | |
|---|---|---|---|
| 3,042,685 A | 7/1962 | Roussel | |
| 2,920,080 A | 1/1965 | Bucourt et al. | |
| 3,625,973 A | 12/1971 | Julia | |
| 3,790,596 A | 2/1974 | Shkilkova et al. | |
| 3,976,639 A | 8/1976 | Batcho et al. | |
| 5,210,215 A | 5/1993 | Politi et al. | |
| 6,001,868 A * | 12/1999 | Firestone et al. | 514/415 |

(Continued)

FOREIGN PATENT DOCUMENTS

| | | |
|---|---|---|
| EP | 0421946 | 4/1991 |
| FR | 1373316 | 9/1964 |

(Continued)

OTHER PUBLICATIONS

Alic, p. 1-11, Multiple myeloma, 2002, www.lifesteps.com/gm/Atoz/ency/multiple_myeloma.jsp.*

(Continued)

*Primary Examiner* — Savitha Rao

(57) ABSTRACT

Indole derivatives, compositions including same, and methods utilizing same for the treatment of amyloid associated diseases, such as type II diabetes mellitus, Alzheimer's dementia or diseases, systemic and localized amyloidosis, and prion-related encephalopathies are provided.

1 Claim, 9 Drawing Sheets

A

B

C

(56) References Cited

U.S. PATENT DOCUMENTS

| | | | |
|---|---|---|---|
| 6,395,768 B1* | 5/2002 | Pappolla et al. | 514/415 |
| 2001/0041732 A1 | 11/2001 | Gurley et al. | |
| 2004/0029830 A1 | 2/2004 | Herbert | |
| 2004/0152672 A1 | 8/2004 | Carson et al. | |
| 2008/0194667 A1 | 8/2008 | Gazit et al. | |
| 2008/0305040 A1* | 12/2008 | Klunk | 424/1.65 |

FOREIGN PATENT DOCUMENTS

| | | |
|---|---|---|
| WO | WO 80/00789 | 1/1980 |
| WO | WO 99/42102 | 8/1999 |
| WO | WO 99/58652 | 11/1999 |
| WO | WO 00/24390 | 5/2000 |
| WO | WO 03/024443 | 3/2003 |
| WO | WO 03/039540 | 5/2003 |
| WO | WO 03/070269 | 8/2003 |
| WO | WO 2005/016339 | 2/2005 |
| WO | WO 2005/085867 | 9/2005 |
| WO | WO 2006/018850 | 2/2006 |
| WO | WO 2006/020681 | 2/2006 |

OTHER PUBLICATIONS

Stella, Valentino J, Expert Opinion of Therapeutic Patents, Prodrugs as therapeutics, 2004 14(3): 277-280.*
Wolff et al. (Burger's Medicinal Chemistry, 5th Ed., vol. 1, pp. 975-977, 1994).*
Testa, Bernard, Biochemical Pharmacology, Prodrug Research: futile or fertile? 68 (2004) 2097-2106.*
Ettmayer, Peter, Medicinal Chemistry, Lessons Learned from Marketed and Investigational Prodrugs, 47(10) (2004) 2394-2404.*
Josefson, British Medical Journal, vol. 325, Jul. 2002, p. 7.*
Papolla et al. (Curr. Med. Chem.—Immun., Endoc. and Metab. Agents, vol. 3, 2003 pp. 33-46.*
Arnao et al. (Biochemistry and Molecular Biology international, vol. 39 (6) , 1996, pp. 1125-1134).*
Response Dated Jun. 29, 2010 to Communication Pursuant to Article 94(3) EPC of Feb. 23, 2010 From the European Patent Office Re.: Application No. 05774727.1.
Beugelmans Database Crossfire Beilstein [Online], Beilstein Institut zur Förderung der Chemischen Wissenschaften, Frankfurt am Main, DE, Database Accession No. 116671 (BRN) Compounds INDOL-2-YL-Methanol & Beugelmans R.: Bulletin de la Société Chimique Française, p. 335-336, 1969.
Communication Pursuant to Article 94(3) EPC Dated Mar. 12, 2008 From the European Patent Office Re.: Application No. 05774727.1.
Communication Pursuant to Article 94(3) EPC Dated Feb. 23, 2010 From the European Patent Office Re.: Application No. 05774727.1.
Communication Pursuant to Article 94(3) EPC Dated Jun. 29, 2009 From the European Patent Office Re.: Application No. 05774727.1.
International Preliminary Report on Patentability Dated Mar. 1, 2007 From the International Bureau of WIPO Re.: Application No. PCT/IL2005/000902.
International Search Report and the Written Opinion Dated Jun. 16, 2006 From the International Searching Authority Re.: Application No. PCT/IL2005/000902.
Notice of Allowance Dated Jan. 25, 2010 From the US Patent and Trademark Office Re.: U.S. Appl. No. 11/660,522.
Alic "Multiple Myeloma", Medical Network Inc., HealthAtoZ.com, 11 P., 2002. Retrieved From the Internet.
Appukkuttan et al. "Microwave Enhanced Formation of Electron Rich Arylboronates", Synlett, 8: 1204-1206, 2003. Figs. Scheme 4, Compounds 5A, 5B, 5C, 5D.

Cherny et al. "The YefM Antitoxin Defines a Family of Natively Unfolded Proteins", The Journal of Biological Chemistry, 279(9): 8252-8261, 2004.
Chyan et al. "Potent Neuroprotective Properties Against the Alzheimer β-Amyloid by an Endogenous Melatonin-Related Indole Structure, Indole-3-Propionic Acid", The Journal of Biological Chemistry, 274(31): 21937-21942, Jul. 30, 1999.
Cohen et al "Inhibition of Amyloid Fibril Formation and Cytotoxicity by Hydroxyindole Derivatives", Biochemistry, 45: 4727-4735, 2006. Abstract, p. 4728, col. 1, Last §, p. 4728, col. 2, § 2, Fig.1, p. 4729, col. 1, p. 4728, col. 1, Last §, p. 4728, col. 2, § 2, Fig.1, p. 4728, col. 1, Last §, p. 4728, col. 2, § 2, Fig.1, 4, p. 4732, col. 2, § 2,3, p. 4733, col. 2, § 4.
Engelberg-Kulka et al. "Bacterial Programmed Cell Death Systems as Targets for Antibiotics", Trends in Microbiology, vol. 12 (2): p. 66-71, 2004.
Grady et al. "Axe—Txe, A Broad-Spectrum Proteic Toxin—Antitoxin System Specified by a Multidrug-Resistant, Clinical Isolate of *Enterococcus faecium*", Molecular Microbiology, vol. 47(5: p. 1419-1432, 2003.
Honma et al. "Use of a Thromboxane A2 Antagonist or Synthase Inhibitor for Treating Central Nervous System Diseases, e.g. Alzheimer Type Dementia." Database WPI, Section Ch. Week 200039, Derwent Publications, Class B05, AN 2000-451668. & WO 00/30683 (Yagami et al.), Jun. 2, 2000. Abstract.
Kiselev "Pharmaceutical Composition for Prophylaxis and Treatment of Uterus Cervix Dysplasia and Cancer and Larynx Papillomatosis and Methods of Prophylaxis and Treatment of Said Sicknesses Based on Thereof", Database WPI, Section Ch, Week 200328, Derwent Publications, Class B02, AN 2003-286683 & RU 2196568 C1 (Kiselev) Jan. 20, 2003. Abstract.
Kon-Ya et al "Indole Derivatives as Potent Inhibitors of Larval Settlement by the Barnacle, Balanus Amphitrite", Bioscience, Biotechnology and Biochemistry, JP, 58(12): 2178-2181, 1994. Compound 102.
Lee et al. "Anti-Diabetic Constituent From the Node of Lotus Rhizome (*Nelumbo nucifera* Gaertn)", Natural Product Sciences, 7(4), 107-109, 2001. p. 108, col. 1, Last §-col. 2, § 1.
Losert et al. "Effect of Indole 3 Alkanecarboxylic Acifs on Glucose Utilization in Rats" Arzneimittel-Forschung/Drug Research, 25(6): 880-887, 1975. p. 880, col. 1, § 6, p. 886, col. 2, § 4, 5, p. 887, col. 1, § 3.
Nakajima "Amine Precursor Therapy: Manipulation of Brain Amine Activity With Precursor Amino Acid", Psychiatry and Clinical Neurosciences, 51(5), 267-274, 1997. p. 269, col. 1, § 2, 3.
Nicolaus "Symbiotic Approach to Drug Design", Decision Making in Drug Research, p. 173-186, 1983.
Agora Health "Chemical Found in Broccoli Can Inhibit Cancer Cell Growth", Agora Health, The Healthier Life, Aug. 1, 2002.
Morshedi et al. "Inhibition of Amyloid Fibrillation of Lysozyme by Indole Derivatives—Possible Mechanism of Action", The FEBS Journal, 274: 6415-6425, 2007.
Official Action Dated Feb. 24, 2009 From the US Patent and Trademark Office Re.: U.S. Appl. No. 11/660,522.
Official Action Dated Sep. 29, 2008 From the US Patent and Trademark Office Re.: U.S. Appl. No. 11/660,522.
Beugelmans Database Crossfire Beilstein [Online], Beilstein Institut zur F?rderung der Chemischen Wissenschaften, Frankfurt am Main, DE, Database Accession No. 116671 (BRN) Compounds INDOL-2-YL-Methanol & Beugelmans R.: Bulletin de la Soci?t? Chimique Fran?aise, p. 335-336, 1969.
Chyan et al. "Potent Neuroprotective Properties Against the Alzheimer ?-Amyloid by An Endogenous Melatonin-Related Indole Structure, Indole-3-Propionic Acid", The Journal of Biological Chemistry, 274(31): 21937-21942, Jul. 30, 1999.

* cited by examiner

Figure 3a
Figure 3b
Beta-Amyloid 1-40 5 µM
192 h
Beta-Amyloid 1-40 5 µM+IC 10 µM
192 h
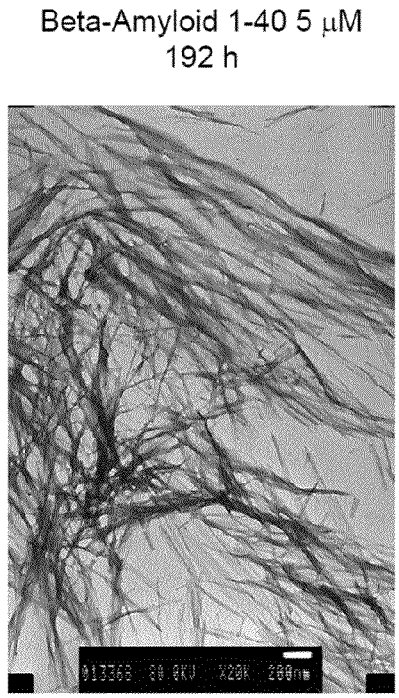
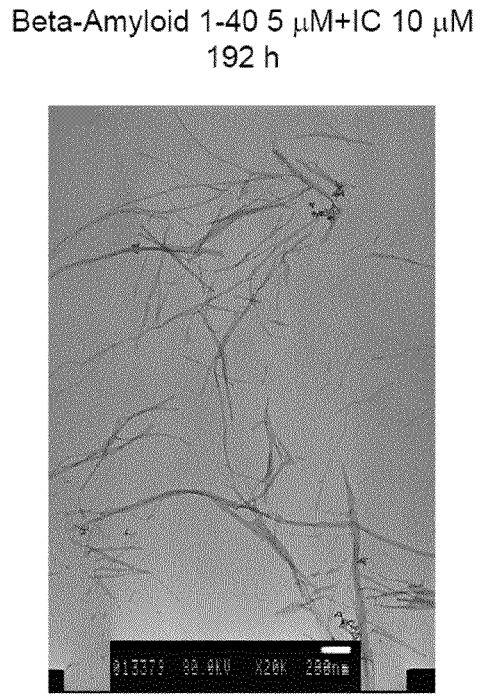

A

B

COMPOSITIONS FOR TREATING AMYLOID ASSOCIATED DISEASES

RELATED APPLICATIONS

This application is a continuation of U.S. patent application Ser. No. 11/660,522, filed Oct. 10, 2007, which is a National Phase of PCT Patent Application No. PCT/IL2005/000902 having International Filing Date of Aug. 18, 2005, which claims the benefit of U.S. Provisional Patent Application Nos. 60/649,574 filed Feb. 4, 2005 and 60/602,635 filed Aug. 19, 2004. The contents of the above applications are all incorporated herein by reference.

FIELD AND BACKGROUND OF THE INVENTION

The present invention relates to compounds, compositions and methods using the same for preventing amyloid fibril formation. More particularly, the present invention relates to indole derivatives, compositions including same, and methods using the same, for the treatment of amyloid associated diseases, such as type II diabetes mellitus, Alzheimer's dementia or diseases, systemic and localized amyloidosis, and prion-related encephalopathies.

Amyloid material deposition (also referred to as amyloid plaque formation) is a central feature of a variety of unrelated pathological conditions including Alzheimer's disease, prion-related encephalopathies, type II diabetes mellitus, familial amyloidosis, secondary amyloidosis, and light-chain amyloidosis.

Amyloid material is composed of a dense network of rigid, nonbranching proteinaceous fibrils of indefinite length that are about 80 to 100 Å in diameter. Amyloid fibrils contain a core structure of polypeptide chains arranged in antiparallel β-pleated sheets lying with their long axes perpendicular to the long axis of the fibril [Both et al. (1997) Nature 385:787-93; Glenner (1980) N. Eng. J. Med. 302:1283-92].

Approximately twenty amyloid fibril proteins have been identified in-vivo and correlated with specific diseases. These proteins share little or no amino acid sequence homology, however the core structure of the amyloid fibrils is essentially the same. This common core structure of amyloid fibrils and the presence of common substances in amyloid deposits suggest that data characterizing a particular form of amyloid material may also be relevant to other forms of amyloid material and thus can be implemented in template design for the development of drugs for use against amyloid associated diseases such as type II diabetes mellitus, Alzheimer's dementia or diseases, and prion-related encephalopathies.

Furthermore, amyloid deposits do not appear to be inert in vivo, but rather are in a dynamic state of turnover and can even regress if the formation of fibrils is halted [Gillmore et al. (1997) Br. J. Haematol. 99:245-56].

Thus, therapies designed to inhibiting the production of amyloid polypeptides or inhibiting amyloidosis may be useful for treating amyloid associated diseases.

Inhibition of the production of amyloid polypeptides: Direct inhibition of the production of amyloid polypeptides may be accomplished, for example, through the use of antisense oligonucleotides, such as against human islet amyloid polypeptide messenger RNA (mRNA). In vitro, the addition of antisense oligonucleotides or the expression of antisense complementary DNA against islet amyloid polypeptide mRNA increases insulin mRNA and protein content of cells, demonstrating the potential effectiveness of this approach [Kulkarni et al. (1996) J. Endocrinol. 151:341-8; Novials et al. (1998) Pancreas 17:182-6]. However, no experimental result demonstrating the in vivo effectiveness of such antisense molecules has been disclosed.

Inhibition of the formation of amyloid fibrils: Amyloid, including islet amyloid, contains potential stabilizing or protective substances, such as serum amyloid P component, apolipoprotein E, and perlecan. Blocking their binding to developing amyloid fibrils could inhibit amyloidogenesis [Kahn et al. (1999) Diabetes 48:241-53], as could treatment with antibodies specific for certain parts of an amyloidogenic protein [Solomon et al. (1997) Proc. Natl. Acad. Sci. USA 94:4109-12].

The following summarizes current attempts to engineer drugs having the capability of destabilizing amyloid structures.

Destabilizing compounds: Heparin sulfate has been identified as a component of all amyloids and has also been implicated in the earliest stages of inflammation associated amyloid induction. Kisilevsky and co-workers (Mature Med. 1:143-148, 1995) described the use of low molecular weight anionic sulfonate or sulfate compounds that interfere with the interaction of heparin sulfate with the inflammation associated amyloid precursor and the β peptide of Alzheimer's disease (AD). Heparin sulfate specifically influences the soluble amyloid precursor (SAA2) to adopt an increased β-sheet structure characteristic of the protein folding pattern of amyloids. These anionic sulfonate or sulfate compounds were shown to inhibit heparin accelerated Aβ fibril formation, and were able to disassemble preformed fibrils in vitro, as monitored by electron micrography. Moreover, these compounds substantially arrested murine splenic inflammation associated amyloid progression in vivo in acute and chronic models. However, the most potent compound [i.e., poly-(vinylsulfonate)] showed acute toxicity. Similar toxicity has been observed with another compound, IDOX (Anthracycline 4'-iodo-4'-deoxy-doxorubicin), which has been observed to induce amyloid resorption in patients with immunoglobin light chain amyloidosis (AL) [Merlini et al. (1995) Proc. Natl. Acad. Sci. USA].

Destabilizing antibodies: Anti-β-amyloid monoclonal antibodies have been shown to be effective in disaggregating β-amyloid plaques and preventing β-amyloid plaque formation in vitro (U.S. Pat. No. 5,688,561). However, no experimental result demonstrating the in vivo effectiveness of such antibodies has been disclosed.

Small molecules: The potential use of small molecules which bind amyloid polypeptide and stabilize the native fold of the protein has been attempted in the case of transthyretin (TTR) protein [Peterson (1998) Proc. Natl. Acad. Sci. USA 95:12965-12960; Oza (1999) Bioorg. Med. Chem. Lett. 9:1-6]. Thus far, it has been demonstrated that molecules such as thyroxine and flufenamic acid are capable of preventing the conformation change, leading to amyloid formation. However, the use of such compounds in animal models has not yet been proven, and might be compromised due to the presence of such compounds in blood, or in proteins other than TTR, which are capable of binding these ligands.

Antioxidants: Another proposed therapy has been the intake of antioxidants in order to avoid oxidative stress and maintain amyloid proteins in their reduced state (i.e., monomers and dimers). The use of sulfite was shown to lead to more stable monomers of TTR protein both in vitro and in vivo [Altland (1999) Neurogenetics 2:183-188]. However, a complete characterization of the antioxidant effect is still not available and the interpretation of results concerning possible therapeutic strategies remains unclear.

Destabilizing peptides: The finding that the addition of synthetic peptides that disrupt the β-pleated sheets ('β-sheet breakers'), thereby dissociating fibrils and preventing amyloidosis [Soto et al. (1998) Nat. Med. 4:822-6,], is particularly promising from a clinical point of view. In that disclosure, it was found that a penta-residue peptide inhibited amyloid beta-protein fibrillogenesis, disassembled preformed fibrils in vitro, and prevented neuronal death induced by fibrils in cell culture. In addition, the beta-sheet breaker peptide significantly reduced amyloid beta-protein deposition in vivo, and completely blocked the formation of amyloid fibrils in a rat brain model of amyloidosis.

Green tea extracts: U.S. patent applications having the Publication Nos. 20020086067 and 20020151506 teach the use of various components of green tea extracts for treating an amyloid disease. While these patent applications teach that these components inhibit amyloid fibril formation, they fail to teach neither a mechanism nor a common structural feature which provides these green tea components with such an activity.

SUMMARY OF THE INVENTION

The present inventor has previously shown that aromatic interactions play a key role in amyloid fibril formation by serving as structural and functional elements that direct molecular recognition and self-assembly and have further shown that such aromatic interactions can be induced by tryptophane containing peptide sequences [Gazit (2002) FASEB J. 16:77-83].

As is well known, tryptophane is an amino acid residue having an indole side-chain. Thus, while conceiving the present invention, it was envisioned that compounds having an aromatic moiety and particularly an indole moiety, which may participate in such aromatic interactions, could efficiently serve as inhibitors of amyloid fibril formation. It was further envisioned that since indoles are known to act as antioxidants [Herraiz et al. (2004) Free Radic Res. 38:323-31], compounds having an indole moiety could serve simultaneously as inhibitors of amyloid fibril formation and as antioxidants and as such may exert synergistic effect in treating amyloid-associated diseases.

While reducing the present invention to practice, the present inventors indeed empirically determined that amyloid formation can be strongly inhibited by indole derivatives, such as indole-3-carbinol (3-hydroxymethyl indole), 3-hydroxyindole, and 4-hydroxyindole, suggesting use of various indole compounds in the treatment of amyloid associated diseases.

Hence, according to one aspect of the present invention there is provided a method of treating an amyloid associated disease in a subject, the method comprising administering to a subject in need thereof, a therapeutically effective amount of a compound having the general formula:

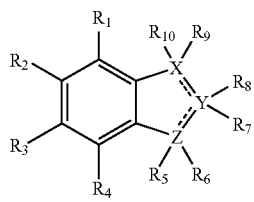

a pharmaceutically acceptable salt thereof, or a prodrug thereof, wherein:
the dashed line denotes a double bond either between X and Y or between Y and Z;

X, Y and Z are each independently selected from the group consisting of carbon and nitrogen, whereas at least one of X, Y, and Z is nitrogen; and $R_1$-$R_{10}$ are each independently selected from the group consisting of hydrogen, lone pair electrons, hydroxy, alkyl, cycloalkyl, phenyl, phenol, hydroxyphenol, dihydroxyphenol, aryl, alkenyl, alkynyl, heteroaryl, heteroalicyclic, halo, alkoxy, aryloxy, thiohydroxy, thioalkoxy, thioaryloxy, C-carboxy, O-carboxy, thiocarboxy, carbonyl, oxo, thiocarbonyl, sulfinyl, and sulfonyl, or absent, or, alternatively, at least two of $R_1$-$R_{10}$ form at least one five- or six-membered aromatic, heteroaromatic, alicyclic or heteroalicyclic ring, thereby treating the amyloid associated disease in the subject.

According to further features in preferred embodiments of the invention described below, each of X and Y is carbon; and Z is nitrogen.

According to still further features in the described preferred embodiments, the double bond is between X and Y.

According to still further features in the described preferred embodiments at least one of $R_1$-$R_{10}$ comprises an electronegative group.

According to still further features in the described preferred embodiments at least one of $R_1$ and $R_9$ comprises an electronegative group.

The electronegative group can be, for example, hydroxy or halo (e.g., chloro, bromo and iodo).

According to still further features in the described preferred embodiments, at least one of $R_1$-$R_{10}$ comprises a hydroxy group.

According to still further features in the described preferred embodiments, the double bond is between X and Y and at least one of $R_1$-$R_{10}$ comprises a hydroxy group.

According to still further features in the described preferred embodiments, at least one of $R_1$ and $R_9$ comprises a hydroxy group.

According to still further features in the described preferred embodiments, at least one of $R_1$ and $R_9$ is a hydroxy group.

According to still further features in the described preferred embodiments, each of $R_2$-$R_5$ and $R_7$ is hydrogen and $R_6$, $R_8$ and $R_{10}$ are absent, the compound being either 3-hydroxyindole or 4-hydroxyindole.

According to still further features in the described preferred embodiments, $R_1$ is hydrogen and $R_9$ is a hydroxy group, the compound being 3-hydroxyindole.

According to still further features in the described preferred embodiments, $R_1$ is a hydroxy group and $R_9$ is hydrogen, the compound being 4-hydroxyindole.

According to still further features in the described preferred embodiments, at least one of $R_1$-$R_{10}$ is a hydroxyalkyl.

According to still further features in the described preferred embodiments, at least one of $R_7$ and $R_9$ is a hydroxyalkyl.

According to still further features in the described preferred embodiments, each of $R_1$-$R_5$ is hydrogen, and $R_6$, $R_8$ and $R_{10}$ are absent.

According to still further features in the described preferred embodiments, the hydroxyalkyl is hydroxymethyl.

According to still further features in the described preferred embodiments, $R_7$ is hydrogen and $R_9$ is hydroxymethyl, the compound being indole-3-carbinol (3-hydroxymethyl indole).

According to still further features in the described preferred embodiments, each $R_7$ and $R_9$ is hydroxyalkyl, the compound being a 2,3-dihydroxyalkyl indole.

According to still further features in the described preferred embodiments, the administering is effected at a concentration of the compound not exceeding 4 mg/kg body weight/hour.

According to still further features in the described preferred embodiments, the administering is effected orally.

According to another aspect of the present invention, there is provided use of the compound described hereinabove, for the manufacture of a medicament identified for the treatment of amyloid associated diseases.

According to another aspect of the present invention there is provided a pharmaceutical composition comprising a therapeutically effective amount of the compound described hereinabove and a pharmaceutically acceptable carrier.

According to further features in the described preferred embodiments, the pharmaceutical composition further comprises an anti-amyloid drug.

According to still further features in the described preferred embodiments, the anti-amyloid drug is selected from the group consisting of an amyloid destabilizing antibody, an amyloid destabilizing peptide and an anti-amyloid small molecule.

According to another aspect of the present invention there is provided an article-of-manufacture comprising a packaging material and a pharmaceutical composition identified for treating amyloid associated diseases being contained within the packaging material, the pharmaceutical composition including, as an active ingredient, the compound described hereinabove, and a pharmaceutically acceptable carrier.

According to another aspect of the present invention there is provided a compound having the above described general formula, with the proviso that the compound is not any one selected from the group consisting of indole, 2-hydroxyindole, 3-hydroxyindole, 4-hydroxyindole, 5-hydroxyindole, 3-methyl indole, indole-3-acetic acid, indole-3-butyric acid, indole-3-carboxylic acid, indole-3-propionic acid, indole-3-ethanol, indole-3-carbinol, and a 2,3-hydroxyalkyl indole.

According to further features in the described preferred embodiments of the compound of the present invention, each of X and Y is carbon; and Z is nitrogen.

According to further features in the described preferred embodiments of the compound of the present invention, the double bond is between X and Y.

According to further features in the described preferred embodiments of the compound of the present invention, at least one of $R_1$-$R_{10}$ comprises a hydroxy group.

According to further features in the described preferred embodiments of the compound of the present invention, at least one of $R_1$-$R_{10}$ is a hydroxyalkyl.

The present invention successfully addresses the shortcomings of the presently known configurations by providing novel compounds and compositions which can be efficiently used for preventing amyloid fibril formation and thus for treating amyloid associated diseases.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 3a-b present electron micrographs showing microstructural features of representative fluorescence assay samples of Aβ 1-40 (per FIG. 2) in the absence (FIG. 3a) and presence (FIG. 3b) of indole-3-carbinol, after attainment of the plateau at about 192 hours, and clearly demonstrating inhibition of β-amyloid fibril formation by the indole-3-carbinol, in accordance with the present embodiments;

DESCRIPTION OF THE PREFERRED EMBODIMENTS

The present invention is of indole derivatives and compositions including same, which can be efficiently used for preventing amyloid fibril formation and thus for the treatment of amyloid associated diseases, such as type II diabetes mellitus, Alzheimer's dementia or diseases, and prion-related encephalopathies.

The principles and operation of the compounds, compositions and methods according to the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Numerous therapeutic approaches for prevention of amyloid fibril formation or disaggreagtion of amyloid material have been described in the prior art. However, current therapeutic approaches are limited by cytotoxicity, non-specificity and delivery barriers.

The present inventors have previously shown that aromatic interactions play a key role in amyloid fibril formation by serving as structural and functional elements that direct molecular recognition and self-assembly [Azriel and Gazit (2001) J. Biol. Chem. 276: 34156-34161; Gazit (2002) FASEB J. 16:77-83]. Consequently, aromatic peptides and, particularly aromatic peptides that include one or more tryptophane residues, were shown to inhibit amyloid fibril formation.

It was therefore envisioned that compounds having an indole moiety, as in tryptophane, can participate in the aromatic interactions described above and would thus inhibit amyloid formation.

Figure 1:
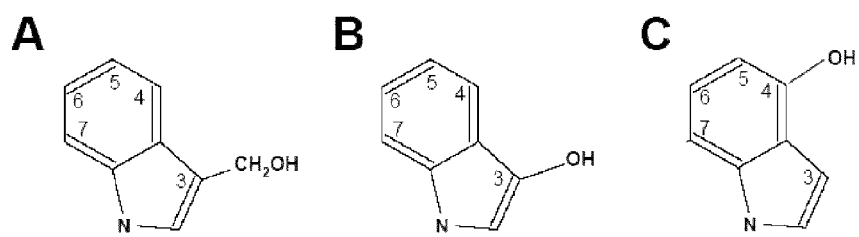
FIGS. 1a-c present the 2D chemical structures of indole-3-carbinol (3-hydroxymethyl indole), 3-hydroxyindole, and 4-hydroxyindole, as exemplary indole derivatives which can be used for implementing the present invention.

While reducing the present invention to practice, the present inventors empirically determined that amyloid formation can be strongly inhibited by indole derivatives, such as indole-3-carbinol (3-hydroxymethyl indole), 3-hydroxyindole, and 4-hydroxyindole, (see, FIG. 1), suggesting use of these compounds in the treatment of amyloid associated diseases.

Indole-3-carbinol is known as a food supplement that can be used in anti-cancer therapy [Donald et al. (2004) Int J Cancer. 111:961-7]. However, the use of indole-3-carbinol, or other indole derivatives, such as 3-hydroxyindole, and 4-hydroxyindole, for inhibiting formation of amyloid fibrils has never been suggested nor practiced hitherto.

An indole derivative, according to the present invention, is represented by the general formula:

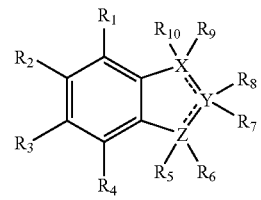

a pharmaceutically acceptable salt thereof, or a prodrug thereof, wherein:

the dashed line denotes a double bond either between X and Y, or, between Y and Z;

X, Y and Z are each independently selected from the group consisting of carbon and nitrogen, whereas at least one of X, Y, and Z is nitrogen; and $R_1$-$R_{10}$ are each independently selected from the group consisting of hydrogen, lone pair electrons, hydroxy, alkyl, cycloalkyl, phenyl, phenol, hydroxyphenol, dihydroxyphenol, aryl, alkenyl, alkynyl, heteroaryl, heteroalicyclic, halo, alkoxy, aryloxy, thiohydroxy, thioalkoxy, thioaryloxy, C-carboxy, O-carboxy, thiocarboxy, carbonyl, oxo, thiocarbonyl, sulfinyl, and sulfonyl, or absent, or, alternatively, at least two of $R_1$-$R_{10}$ form at least one five- or six-membered aromatic, heteroaromatic, alicyclic or heteroalicyclic ring.

As used herein, the term 'alkyl' refers to a saturated aliphatic hydrocarbon including straight chain and branched chain groups. Preferably, the alkyl group has 1 to 20 carbon atoms. Whenever a numerical range; e.g., '1-20', is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 4 carbon atoms. The alkyl group may be substituted or unsubstituted. When substituted, the substituent group can be, for example, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azo, sulfonyl, sulfinyl, sulfonamide, phosphonyl, phosphinyl, phosphonium, ketoester, carbonyl, thiocarbonyl, ester, ether, carboxy, thiocarboxy, thioether, thiocarbamate, urea, thiourea, O-carbamyl, N-carbamyl, O-thiocarbamyl, N-thiocarbamyl, C-amido, N-amido, C-carboxy, O-carboxy, sulfonamido, trihalomethanesulfonamido, guanyl, guanidino, and amino, as these terms are defined hereinbelow.

As used herein, the term 'hydroxyalkyl' refers to an alkyl, as defined hereinabove, which is further substituted by one or more hydroxy groups. In the compound including two or more carbon atoms and two or more hydroxy groups, then each hydroxy group can be on the same carbon atom or on different carbon atoms. The hydroxyalkyl may be additionally substituted or unsubstituted. When substituted, the substituent group can be, for example, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azo, sulfonyl, sulfinyl, sulfonamide, phosphonyl, phosphinyl, phosphonium, ketoester, carbonyl, thiocarbonyl, ester, ether, carboxy, thiocarboxy, thioether, thiocarbamate, urea, thiourea, O-carbamyl, N-carbamyl, O-thiocarbamyl, N-thiocarbamyl, C-amido, N-amido, C-carboxy, O-carboxy, sulfonamido, trihalomethanesulfonamido, guanyl, guanidino, and amino, as these terms are defined herein.

A 'cycloalkyl' group refers to an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane. A cycloalkyl group may be substituted or unsubstituted. When substituted, the substituent group can be, for example, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azo, sulfonyl, sulfinyl, sulfonamide, phosphonyl, phosphinyl, phosphonium, ketoester, carbonyl, thiocarbonyl, ester, ether, carboxy, thiocarboxy, thioether, thiocarbamate, urea, thiourea, O-carbamyl, N-carbamyl, O-thiocarbamyl, N-thiocarbamyl, C-amido, N-amido, C-carboxy, O-carboxy, sulfonamido, trihalomethanesulfonamido, guanyl, guanidino, and amino, as these terms are defined hereinbelow.

A 'hydroxy' group refers to an —OH group.

An 'alkenyl' group refers to an alkyl group, as defined hereinabove, which consists of at least two carbon atoms and at least one carbon-carbon double bond.

An 'alkynyl' group refers to an alkyl group, as defined hereinabove, which consists of at least two carbon atoms and at least one carbon-carbon triple bond.

An 'aryl' group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted. When substituted, the substituent group can be, for example, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azo, sulfonyl, sulfinyl, sulfonamide, phosphonyl, phosphinyl, phosphonium, ketoester, carbonyl, thiocarbonyl, ester, ether, carboxy, thiocarboxy, thioether, thiocarbamate, urea, thiourea, O-carbamyl, N-carbamyl, O-thiocarbamyl, N-thiocarbamyl, C-amido, N-amido, C-carboxy, O-carboxy, sulfonamido, trihalomethanesulfonamido, guanyl, guanidino, and amino, as these terms are defined herein.

As used herein, the term 'phenol' refers to a phenyl substituted by an hydroxy group. The phenol group may be substituted or unsubstituted. When substituted, the substituent group can be, for example, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azo, sulfonyl, sulfinyl, sulfonamide, phosphonyl, phosphinyl, phosphonium, ketoester, carbonyl, thiocarbonyl, ester, ether, carboxy, thiocarboxy, thioether, thiocarbamate, urea, thiourea, O-carbamyl, N-carbamyl, O-thiocarbamyl, N-thiocarbamyl, C-amido, N-amido, C-carboxy, O-carboxy, sulfonamido, trihalomethanesulfonamido, guanyl, guanidino, and amino, as these terms are defined herein.

As used herein, the term 'hydroxyphenol', which also encompasses the term 'dihydroxyphenol' refers to a phenol, as defined hereinabove, which is further substituted by one or more additional hydroxy groups. The additional hydroxy groups can be at the para, ortho and/or meta positions with respect to the hydroxy group of the phenol. The hydroxyphenol may be additionally substituted or unsubstituted. When substituted, the substituent group can be, for example, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azo, sulfonyl, sulfinyl, sulfonamide, phosphonyl, phosphinyl, phosphonium, ketoester, carbonyl, thiocarbonyl, ester, ether, carboxy, thiocarboxy, thioether, thiocarbamate, urea, thiourea, O-carbamyl, N-carbamyl, O-thiocarbamyl, N-thiocarbamyl, C-amido, N-amido, C-carboxy, O-carboxy, sulfonamido, trihalomethanesulfonamido, guanyl, guanidino, and amino, as these terms are defined herein.

A 'heteroaryl' group refers to a monocyclic or fused ring (i.e., rings which share an adjacent pair of atoms) group having in the ring(s) one or more hetero-atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted. When substituted, the substituent group can be, for example, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azo, sulfonyl, sulfinyl, sulfonamide, phosphonyl, phosphinyl, phosphonium, ketoester, carbonyl, thiocarbonyl, ester, ether, carboxy, thiocarboxy, thioether, thiocarbamate, urea, thiourea, O-carbamyl, N-carbamyl, O-thiocarbamyl, N-thiocarbamyl, C-amido, N-amido, C-carboxy, O-carboxy, sulfonamido, trihalomethanesulfonamido, guanyl, guanidino, and amino, as these terms are defined herein.

A 'heteroalicyclic' group refers to a monocyclic or fused ring group having in the ring(s) one or more hetero-atoms such as nitrogen, oxygen and sulfur. The rings may also have one or more double bonds. However, the rings do not have a completely conjugated pi-electron system. The heteroalicyclic may be substituted or unsubstituted. When substituted, the substituted group can be, for example, lone pair electrons, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azo, sulfonyl, sulfinyl, sulfonamide, phosphonyl, phosphinyl, phosphonium, ketoester, carbonyl, thiocarbonyl, ester, ether, carboxy, thiocarboxy, thioether, thiocarbamate, urea, thiourea, O-carbamyl, N-carbamyl, O-thiocarbamyl, N-thiocarbamyl, C-amido, N-amido, C-carboxy, O-carboxy, sulfonamido, trihalomethanesulfonamido, guanyl, guanidino, and amino, as these terms are defined herein. Representative examples are piperidine, piperazine, tetrahydrofurane, tetrahydropyrane, morpholino and the like.

A 'halo' group refers to fluoro, chloro, bromo or iodo.

An 'alkoxy' group refers to both an —O-alkyl and an —O-cycloalkyl group, as defined herein.

An 'aryloxy' group refers to both an —O-aryl and an —O-heteroaryl group, as defined herein.

A 'thiohydroxy' group refers to a —SH group.

A 'thioalkoxy' group refers to both an —S-alkyl group, and an —S-cycloalkyl group, as defined herein.

A 'thioaryloxy' group refers to both an —S-aryl and an —S-heteroaryl group, as defined herein.

An 'oxo' group refers to an =O group.

A 'carbonyl' group refers to a —C(=O)—R' group, where R' is hydrogen, alkyl, alkenyl, cycloalkyl, aryl, heteroaryl (bonded through a ring carbon) or heteroalicyclic (bonded through a ring carbon) as defined herein.

A 'thiocarbonyl' group refers to a —C(=S)—R' group, where R' is as defined herein for R'.

A 'C-carboxy' group refers to a —C(=O)—O—R' groups, where R' is as defined herein.

An 'O-carboxy' group refers to a R'C(=O)—O— group, where R' is as defined herein.

A 'thiocarboxy' group refers to a R'C(=O)—S— group, where R' is as defined herein.

A 'sulfinyl' group refers to an —S(=O)—R' group, where R' is as defined herein.

A 'sulfonyl' group refers to an —S(=O)$_2$—R' group, where R' is as defined herein.

A 'trihalomethyl' group refers to a —CX group wherein X is a halo group as defined herein.

A 'trihalomethanesulfonyl' group refers to a X$_3$CS(=O)$_2$— group wherein X is a halo group as defined herein.

A 'S-sulfonamido' group refers to a —S(=O)$_2$—NR'R" group, with R' and R" as defined herein.

A 'N-sulfonamido' group refers to n R'S(=O)$_2$—NR" group, where R' and R" are as defined herein.

A 'trihalomethanesulfonamido' group refers to an X$_3$CS(=O)$_2$NR'— group, where R' and X are as defined herein.

An 'O-carbamyl' group refers to an —OC(=O)—NR'R" group, where R' and R" are as defined herein.

A 'N-carbamyl' group refers to an R"OC(=O)—NR'— group, where R' and R" are as defined herein.

An 'O-thiocarbamyl' group refers to an —OC(=S)—NR'R" group, where R' and R" are as defined herein.

A 'N-thiocarbamyl' group refers to an R"OC(=S)NR'— group, where R' and R" are as defined herein.

An 'amino' group refers to an —NR'R" group where R' and R" are as defined herein.

A 'C-amido' group refers to a —C(=O)—NR'R" group, where R' and R" are as defined herein.

A 'N-amido' group refers to an R'C(=O)—NR" group, where R' and R" are as defined herein.

An 'urea' group refers to an —NR'C(=O)—NR"R'" group, where R' and R" are as defined herein and R'" is defined as either R' or R".

A 'guanidino' group refers to an —R'NC(=N)—NR"R'" group, where R', R" and R'" are as defined herein.

A 'guanyl' group refers to an R'R"NC(=N)— group, where R' and R" are as defined herein.

A 'nitro' group refers to an —NO$_2$ group.

A 'cyano' group refers to a —C≡N group.

An 'azo' group refers to a —N=N group.

The term 'phosphonyl' describes a —O—P(=O)(OR')— group, with R' as defined hereinabove.

The term 'phosphinyl' describes a —PR'— group, with R' as defined hereinabove.

The term 'phosphonium' is a —P$^+$R'R", where R' and R" are as defined hereinabove.

Thus, preferred compounds which conform to the above illustratively described general formula, and which can be used for implementing the present invention, are therefore indole derivatives, being compounds having an aromatic ring fused to a heterocyclic ring having at least one nitrogen atom. The parent compound, indole, is a heteroaromatic compound having a phenyl ring fused to a pyrrole ring and thus comprises a completely conjugated pi-electron system.

However, an indole derivative, according to the present invention, encompasses any aromatic moiety that is fused to a heterocyclic ring containing one or more nitrogen atoms (for example, one, two or three nitrogen atoms). Depending of the location of the pi-electrons of the double bond (between X and Y or Y and Z, see, the formula above) and the nature of the ring atoms (carbon and/or nitrogen), the electronic structure of an indole derivative according to the present invention can include either a partially or completely conjugated pi-electron system.

Thus, an indole derivative, according to the present invention, encompasses, for example, substituted or unsubstituted indoles, substituted or unsubstituted purines, substituted or unsubstituted carbazoles and substituted or unsubstituted phenyl ring fused to a substituted or unsubstituted imidazole, pyrazole, thiazine, and the like, with substituted or unsubstituted indoles being the presently preferred indole derivatives.

Thus, preferred compounds which can be used for implementing the present invention, are compounds which have the above illustratively described general formula, wherein each of X and Y is carbon, and Z is nitrogen, whereby the double bond (dashed line) is preferably between X and Y.

Further preferred compounds for implementing the present invention, are compounds which have the above illustratively described general formula, wherein one or more of $R_1$-$R_{10}$ comprises an electronegative group. In such compounds, the one or more electronegative groups are directly or indirectly attached to the indole derivative skeleton.

As used herein, the phrase "electronegative group" describes a chemical moiety or atom which, when bound to another chemical moiety or atom, has at least a partial electronegative charge.

As can be seen in the Examples section that follows, indole derivatives that include an electronegative group such as hydroxy were found to exhibit superior inhibitory activity and therapeutic effect, as compared with other tested non-hyroxy containing indole derivatives. Without being bound to any particular theory, it is assumed that at least some of the beneficial effects of such compounds can be attributed to the modulation of the electrical properties of the indole derivatives, induced by such an electronegative group.

Representative examples of electronegative groups that can be beneficially included in the indole derivatives described herein include, without limitation, chemical moieties or atoms that include a halogen atom, an oxygen atom, a sulfur atom, a nitrogen atom, a phosphor atom and the like, as well as chemical moieties that include a carbon atom adjacent to an electropositive group such as a metal. These include, for example, a halo group, a hydroxy group, a thiohydroxy group, an amine group, a nitro group, a nitrile group, a sulfonate group, a phosphonate group and the like.

Preferred electronegative groups according to the present embodiments include halo and hydroxy, as these terms are defined herein.

Thus, particularly preferred compounds which can be used for implementing the present invention, are indoles substituted by an electronegative group such as a hydroxy and/or halo group and are therefore compounds which have the above illustratively described general formula, wherein each of X and Y is carbon, and Z is nitrogen, the double bond (dashed line) is between X and Y, and at least one of $R_1$-$R_{10}$ is a hydroxy and/or halo group. Preferably, in such hydroxy and/or halo group containing compounds, at least one of $R_1$, $R_3$, $R_4$, and $R_9$ is a hydroxy and/or halo group, and more preferably, $R_1$ and/or $R_9$ is a hydroxy and/or halo group. More preferably, in such hydroxy group containing compounds, each of $R_2$-$R_5$ and $R_7$ is hydrogen and $R_6$, $R_8$ and $R_{10}$ are absent.

A representative example of such a halo containing compound is 3-haloindole, such that in the general formula, $R_1$ is hydrogen and $R_9$ is halo, wherein the halo can be chloro, bromo and iodo. Another representative example of such a halo containing compound is 4-haloindole, such that in the general formula, $R_1$ is halo and $R_9$ is hydrogen, wherein the halo can be chloro, bromo and iodo.

Additional particularly preferred compounds which can be used for implementing the present invention, are indoles substituted by one or more halo-containing groups and are therefore compounds which have the above illustratively described general formula, wherein each of X and Y is carbon, and Z is nitrogen, the double bond (dashed line) is between X and Y, and at least one of $R_1$-$R_{10}$ is a halo-containing group, as detailed hereinabove. The halo-containing group can be, for example, alkyl, alkenyl, cycloalkyl or aryl being substituted by one or more halo groups.

Preferably, in such halo containing compounds, at least one of $R_7$ and $R_9$ is a halo containing group, as detailed hereinabove. More preferably, in such halo containing compounds, each of $R_1$-$R_5$ is hydrogen, and $R_6$, $R_8$ and $R_{10}$ are absent.

As mentioned hereinabove and is further demonstrated and discussed in the Examples section that follows, indole derivatives that include a hydroxy group where found to exhibit a superior inhibitory activity and therapeutic effect.

Thus, preferred compounds for implementing the present invention, are compounds which have the above illustratively described general formula, wherein one or more of $R_1$-$R_{10}$ comprises a hydroxy group. In such compounds, the one or more hydroxy groups are directly or indirectly attached to the indole derivative skeleton, such that at least one of $R_1$-$R_{10}$ is either hydroxy or, for example, a hydroxyalkyl, as defined hereinabove.

Particularly preferred compounds which can be used for implementing the present invention, are indoles substituted by a hydroxy group and are therefore compounds which have the above illustratively described general formula, wherein each of X and Y is carbon, and Z is nitrogen, the double bond (dashed line) is between X and Y, and at least one of $R_1$-$R_{10}$ is a hydroxy group. Preferably, in such hydroxy group containing compounds, at least one of $R_1$, $R_3$, $R_4$, and $R_9$ is a hydroxy group, and more preferably, $R_1$ or $R_9$ is a hydroxy group. More preferably, in such hydroxy group containing compounds, each of $R_2$-$R_5$ and $R_7$ is hydrogen and $R_6$, $R_8$ and $R_{10}$ are absent.

A representative example of such a hydroxy containing compound is 3-hydroxyindole, such that in the general formula, $R_1$ is hydrogen and $R_9$ is the hydroxy group. Another representative example of such a hydroxy containing compound is 4-hydroxyindole, such that in the general formula, $R_1$ is the hydroxy group and $R_9$ is hydrogen.

Additional particularly preferred compounds which can be used for implementing the present invention, are indoles substituted by one or more hydroxyalkyl groups and are therefore compounds which have the above illustratively described general formula, wherein each of X and Y is carbon, and Z is nitrogen, the double bond (dashed line) is between X and Y, and at least one of $R_1$-$R_{10}$ is a hydroxyalkyl. Preferably, in such hydroxyalkyl containing compounds, at least one of $R_7$ and $R_9$ is a hydroxyalkyl. More preferably, in such hydroxyalkyl containing compounds, each of $R_1$-$R_5$ is hydrogen, and $R_6$, $R_8$ and $R_{10}$ are absent. More preferably, in such hydroxyalkyl containing compounds, at least one of $R_7$ and $R_9$ is a hydroxymethyl type of hydroxyalkyl.

A representative example of such a hydroxyalkyl containing compound is indole-3-carbinol (3-hydroxymethyl indole), such that in the general formula, $R_7$ is hydrogen and $R_9$ is a hydroxymethyl.

Another representative example of such a hydroxyalkyl containing compound is a 2,3-dihydroxyalkyl indole, such that in the general formula above, each $R_7$ and $R_9$ is a hydroxyalkyl.

As described in detail in the Examples below, while reducing the present invention to practice, the present inventors empirically determined that amyloid formation can be strongly inhibited by each of the indole derivatives indole-3-carbinol, 3-hydroxyindole, or 4-hydroxyindole, individually. This empirical determination confirms the inventive concept that compounds having an indole moiety, as in tryptophan, would participate in the aromatic interactions described above and would thus inhibit amyloid formation, thereby suggesting the use of these compounds in the treatment of amyloid associated diseases.

Without being bound to any particular theory, it is assumed that the hydroxy group, by being an electron-donor group, alters the electron density and the negative charge on the benzopyrrole ring. Additionally, the hydroxy group is capable of interacting with various moieties in the polypeptide by a means of hydrogen bonds. The position of the hydroxyl group is also of key importance. Thus, while the amyloid formation inhibitory mechanism of the indole derivatives described herein remains unclear, it is assumed that the hydroxyl group interacts with the backbone of the peptides, and prevents the occurrence of $\pi$-stacking interactions between the peptides by providing a different electron density and a negative charge of the benzopyrrole and thus the extension of the fibrillogenesis process is blocked.

Thus, according to a main aspect of the present invention, there is provision of a method of treating an amyloid associated disease in a subject. The method includes administering to a subject in need thereof, a therapeutically effective amount of the compound described hereinabove, a pharmaceutically acceptable salt thereof, or a prodrug thereof, thereby treating the amyloid associated disease in the subject.

Preferred individual subjects according to the present invention are mammals such as canines, felines, ovines, porcines, equines, and bovines. Preferably the individual subjects according to the present invention are humans.

The term 'treating' refers to reducing or preventing amyloid plaque formation, or substantially decreasing plaque occurrence in an affected tissue. The phrase 'amyloid plaque' refers to fibrillar amyloid as well as aggregated but not fibrillar amyloid, hereinafter 'protofibrillar amyloid', which may be pathogenic as well [see Anaguiano et al. (2002) Biochemistry 41:11338-43].

Amyloid associated diseases treated according to the present invention include, but are not limited to, type II diabetes mellitus, Alzheimer's disease (AD), early onset Alzheimer's disease, late onset Alzheimer's disease, presymptomatic Alzheimer's disease, Parkinson's disease, SAA amyloidosis, hereditary Icelandic syndrome, multiple myeloma, medullary carcinoma, aortic medical carcinoma, Insulin injection amyloidosis, prion-systematic amyloidosis, choronic inflammation amyloidosis, Huntington's disease, senile systemic amyloidosis, pituitary gland amyloidosis, Hereditary renal amyloidosis, familial British dementia, Finnish hereditary amyloidosis, familial non-neuropathic amyloidosis [Gazit (2002) Curr. Med. Chem. 9:1667-1675] and prion diseases including scrapie of sheep and goats and bovine spongiform encephalopathy (BSE) of cattle [Wilesmith and Wells (1991) Curr Top Microbiol Immunol 172: 21-38] and human prion diseases including (i) kuru, (ii) Creutzfeldt-Jakob Disease (CJD), (iii) Gerstmann-Streussler-Sheinker Disease (GSS), and (iv) fatal familial insomnia (FFI) [Gajdusek (1977) Science 197: 943-960; Medori, Tritschler et al. (1992) N Engl J Med 326: 444-449].

The compounds described hereinabove can be administered or otherwise utilized in this and other aspects of the present invention, either as is, or as a pharmaceutically acceptable salt, or a prodrug thereof.

The term 'prodrug' refers to an agent, which is converted into the active compound (the active parent drug) in vivo. Prodrugs are typically useful for facilitating the administration of the parent drug. They may, for instance, be bioavailable by oral administration whereas the parent drug is not. The prodrug may also have improved solubility as compared with the parent drug in pharmaceutical compositions. Prodrugs are also often used to achieve a sustained release of the active compound in vivo. An example, without limitation, of a prodrug would be a compound of the present invention, having one or more phenol moieties, which is administered as an ester (the 'prodrug'). Such a prodrug is hydrolysed in vivo, to thereby provide the free compound (the parent drug). The selected ester may affect both the solubility characteristics and the hydrolysis rate of the prodrug.

The phrase 'pharmaceutically acceptable salt' refers to a charged species of the parent compound and its counter ion, which is typically used to modify the solubility characteristics of the parent compound and/or to reduce any significant irritation to an organism by the parent compound, while not abrogating the biological activity and properties of the administered compound. An example, without limitation, of a pharmaceutically acceptable salt would be an alkoxide anion ($RO^-$, where R is alkyl or cycloalkyl as defined hereinabove) and a cation such as, but not limited to, ammonium, sodium, potassium and the like.

Preferably, the compound of the present invention is administered at a concentration not exceeding 4 mg/kg×hr.

It will be appreciated that treatment of amyloid associated diseases according to the present invention may be combined with other treatment methods known in the art (i.e., combination therapy). Thus, compounds of the present invention may be co-administered (simultaneously or separately) with additional anti-amyloid drugs. Examples of such anti-amyloid drugs include, but are not limited to, amyloid destabilizing antibodies, amyloid destabilizing peptides and anti-amyloid small molecules (further details on such drugs are provided in the preceding Background section).

According to another aspect of the present invention, there is provided use of the indole derivatives described above for the manufacture of a medicament identified for the treatment of amyloid associated diseases.

According to still another aspect of the present invention there is provided a pharmaceutical composition including a therapeutically effective amount of the compound described hereinabove, and a pharmaceutically acceptable carrier.

Accordingly, the compounds of the present invention can be provided to an individual per se, or as part of a pharmaceutical composition where it is mixed with a pharmaceutically acceptable carrier.

As used herein a 'pharmaceutical composition' refers to a preparation of one or more of the active ingredients described herein with other chemical components such as physiologically suitable carriers and excipients. The purpose of a pharmaceutical composition is to facilitate administration of a compound to the subject treated.

Herein the term 'active ingredient' refers to the compound, which is accountable for the biological effect.

Hereinafter, the phrases 'physiologically acceptable carrier' and 'pharmaceutically acceptable carrier' which may be interchangeably used refer to a carrier or a diluent that does not cause significant irritation to the subject and does not abrogate the biological activity and properties of the administered compound. Preferred carriers of the pharmaceutical composition of the present invention include, but are not limited to, polyethylene glycol (PEG), a biocompatible polymer with a wide range of solubility in both organic and aqueous media (Mutter et al. (1979).

Herein the term 'excipient' refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in 'Remington's Pharmaceutical Sciences,' Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, inrtaperitoneal, intranasal, or intraocular injections.

Alternately, one may administer a preparation in a local rather than systemic manner, for example, via injection of the preparation directly into a specific region of a patient's body.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the invention may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The preparations described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The preparation of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of disease or prolong the survival of the subject being treated.

Determination of a therapeutically effective amount is well within the capability of those skilled in the art.

For any preparation used in the methods of the invention, the therapeutically effective amount or dose can be estimated initially from in vitro assays. For example, a dose can be formulated in animal models and such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. [See e.g., Fingl, et al., (1975) "The Pharmacological Basis of Therapeutics", Ch. 1 p. 1].

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions including the preparation of the present invention formulated in a compatible pharmaceutical carrier may also be prepared, placed in an appropriate container, and labeled for treatment of an indicated condition.

According to another aspect of the present invention, there is provided an article-of-manufacture including a packaging material and a pharmaceutical composition identified for treating amyloid associated diseases being contained within the packaging material, the pharmaceutical composition including, as an active ingredient, the compound described hereinabove, and a pharmaceutically acceptable carrier.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

It is to be fully understood that the present invention further encompasses all of the compounds described hereinabove, in accordance with the above illustratively described general formula.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non-limiting fashion.

Example 1

Materials and Experimental Methods

Peptides and Chemicals:
Recombinant β-amyloid (Aβ 1-40, >98% pure) polypeptide was purchased from rPeptide (Athens Ga., USA). Indole-3-carbinol (FIG. 1) was purchased from Sigma. All reagents were of analytical grade.

Thioflavin T Fluorescence Assay:
Fibrillization of Aβ 1-40 polypeptide was monitored using a Thioflavin T (ThT) dye binding assay. Aβ 1-40 stock solution was diluted to a final concentration of 5 µM polypeptide in 100 mM NaCl, 10 mM sodium phosphate buffer (pH 7.4), without and with addition of the indole-3-carbinol inhibitor (10 µM). For each measurement, ThT was added to a 0.1 ml sample, to give a final concentration of 0.3 µM ThT and 0.4 µM Aβ 1-40 polypeptide. Fluorescence measurements, made after addition of the ThT solution to each sample at 37° C., were carried out using a Jobin Yvon FluoroMax-3 spectrometer (excitation 450 nm, 2.5 nm slit; emission 480 nm, 5 nm slit, integration time of 1 second). Background was subtracted from each sample.

Transmission Electron Microscopy (TEM) Measurements:
10 µl samples from the ThT fluorescence assay were placed on 400-mesh copper grids (SPI supplies, West Chester Pa.) covered by carbon stabilized Formvar film. After 1 minute, excess fluid was removed, and the grids were negatively stained with 2% uranyl acetate in water for another two minutes. Microstructural features of the samples were viewed using a JEOL 1200EX electron microscope operating at 80 kV.

EXPERIMENTAL RESULTS

The results obtained in this example clearly show that indole-3-carbinol, as an exemplary indole derivative according to the present invention, effectively inhibits formation of β-amyloid polypeptide fibrils.

The level of amyloid formation was detected using the above described Thioflavin T (ThT) dye binding assay. Fluorescence (intensity, measured in units of cps (counts per second)) of the ThT bound Aβ 1-40 polypeptide, in the absence and in the presence of 10 µM indole-3-carbinol, was monitored over time, for up to about 350 hours. The results, representing a mean of two independent measurements, are graphically presented in FIG. 2.

Figure 2:
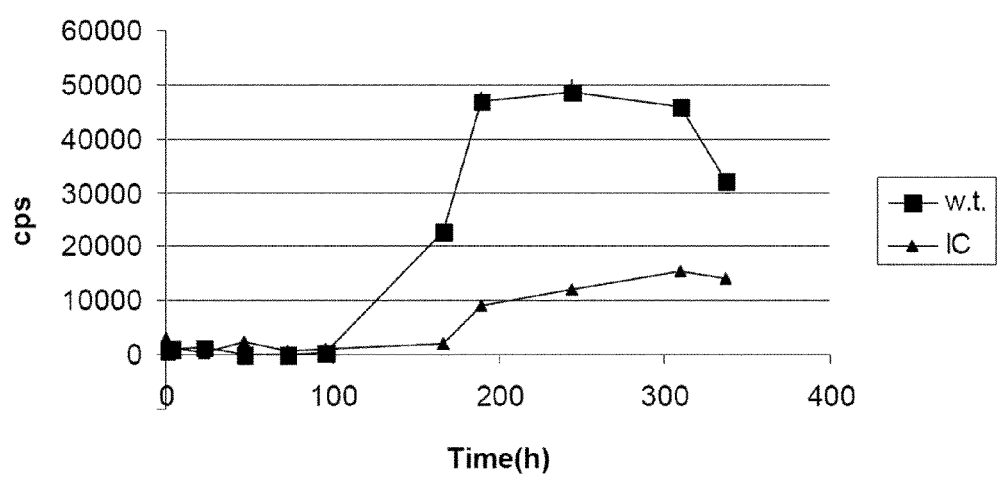
FIG. 2 presents comparative plots illustrating inhibition of β-amyloid fibril formation by indole-3-carbinol, as observed by monitoring fluorescence measurements during a Thioflavin T (ThT) fluorescence binding assay of Aβ 1-40 polypeptide samples in the absence (squares) and presence (triangles) of the indole-3-carbinol, in accordance with the present embodiments.

As is shown in FIG. 2, Aβ 1-40 polypeptide without the indole-3-carbinol (squares) displayed a typical lag-phase of about 100 hours, followed by a rapid increase in fluorescence that reached a plateau after about 200 hours. In the presence of 10 µM indole-3-carbinol (triangles), following about 100 hours, significantly lower levels of fluorescence were detected for the remaining duration of the assay. The lag-time appeared to be significantly extended and the attainment of a plateau was only after about 300 hours. Furthermore, the level of fluorescence at the plateau in the presence of indole-3-carbinol was about a third of the value as compared to that of the non-inhibited Aβ 1-40 polypeptide.

In order to obtain insight into the mechanism of inhibiting formation of β-amyloidpolypeptide type of amyloid fibrils, representative samples taken from the ThT fluorescence assay measurements described above after attainment of the plateau (at about 192 hours, FIG. 2), in the absence or presence of indole-3-carbinol, were viewed using electron microscopy.

The obtained micrographs, presented in FIGS. 3a and 3b demonstrated that distinct and well defined amyloid fibers were present in samples of Aβ 1-40 polypeptide in the absence of indole-3-carbino (FIG. 3a), while, by strong contrast, when indole-3-carbinol was present as an inhibitor in the Aβ 1-40 polypeptide sample, significantly shorter and less dense fiber type material was observed (FIG. 3b). The overall amount of aggregated fibrous material on the electron microscope grid appeared to be significantly lower in the presence of the indole-3-carbinol compound.

Example 2

Materials and Experimental Methods

Aβ peptides:
Aβ solutions: Synthetic lyophilized β-amyloid polypeptides (Aβ 1-40 and Aβ 1-42, >98% pure) were purchased from Bachem (Bubendorf, Switzerland). A 100 µM Aβ stock solution was prepared by dissolving Aβ1-40 or Aβ1-42 in dimethylsulfoxide (DMSO) and sonicating the resulting solution during 1 minute to avoid pre-aggregation. Aβ solutions were prepared by immediate dilution with 10 mM phosphate-buffered saline (100 mM NaCl, 0.5 mM EDTA, pH 7.4) to a final concentration of 10 µM (containing 10% (v/v) DMSO).

Indole derivatives: The following indole derivatives were obtained from Sigma-Aldrich Inc.: Indole-3-carbynol, Tryptamine, 5-nitroindole, 7-methylindole, 5-methylindole, 3-methylindole, indole-3-butyric acid, indole-3-acetic acid, indole-6-carboxylic acid, indole-5-carboxylic acid, indole-3-carboxylic acid, indole-2-carboxylic acid, 2-indolinone, 3-hydroxyindole, 4-hydroxyindole, 5-hydroxyindole, Fmoc-D-Trp, Boc-L-Trp-OH, CBZ-D-Tryptophanamide, CBZ-L-Tryptophanamide, L-5-hydroxytryptophan, D-Tryptophan, L-Tryptophan, indole-3-propionic acid indole-3-ethanol, indole, Nα-Boc-D-Trp, Nα-Boc-L-Trp, Fmoc-Trp-OH.

Indole derivatives stock solutions were prepared by dissolving an indole derivative in DMSO, so as to achieve a concentration of 20 mM and then diluting the solution with 10 mM PBS buffer (100 mM NaCl, 0.5 mM EDTA, pH 7.4) to a final concentration of 100 µM (containing 0.5% (v/v) DMSO).

Thioflavin T fluorescence assay: Fibrillization of Aβ 1-42 polypeptide was monitored using a Thioflavin T (ThT) dye binding assay. A 10 µM Aβ solution (either Aβ1-40 or Aβ1-42) was prepared as described above and was immediately mixed with the indole derivative stock solutions (100 µM), so as to achieve a final concentration of 5 µM for Aβ and various concentrations of the indole derivative. For each measurement, ThT was added to a 0.1 ml sample, to give a final concentration of 0.3 μM ThT and 0.4 μM Aβ. The samples were incubated at 37° C. Fluorescence measurements, made after addition of the ThT solution to each sample at 37° C., were carried out using a Jobin Yvon FluoroMax-3 spectrometer (excitation 450 nm, 2.5 nm slit; emission 480 nm, 5 nm slit, integration time of 1 second). Background was subtracted from each sample. Each experiment was repeated in quadruplicate.

Transmission Electron microscopy (TEM): A 10 μl sample of the ThT fluorescence assay was placed on a 400 mesh copper grid covered by carbon-stabilized Formvar film (SPI Supplies, West Chester, Pa.). After 1.5 minutes, excess fluid was removed and the grids were negatively stained for 2 minutes with 10 μl of 2% uranyl acetate solution. Excess fluid was removed and the samples were viewed using a JEOL 1200EX electron microscope operating at 80 kV.

Atomic force microscopy (AFM): For each experiment, a 60 μl sample of was taken for AFM measurement at three different time points correlating to the amyloidogenic kinetic curve, as detailed hereinafter. The sample was centrifuged for 1.5 minutes at 13,000 rpm and 40 μl of the supernatant was removed. The remaining 20 μl droplet of the solution was re-suspended and deposited onto freshly cleaved mica for 1.5 minutes. The substrate was washed with 160 μl of double-distilled $H_2O$ to reduce background and to eliminate salts and buffer contaminants. The mica samples were then dried at room temperature. At least four regions of the mica surface were examined to ensure that similar structures existed throughout the sample. AFM images were obtained using a Veeco NanoScope IV MultiMode AFM (Digital Instruments, Santa Barbara, USA) in tapping mode. Measurements were performed at a resonance frequency of about 321.4 kHz.

EXPERIMENTAL RESULTS

The results obtained in this example clearly show that various exemplary indole derivatives, according to the present embodiments, effectively inhibit formation of β-amyloid polypeptide fibrils.

Inhibition of amyloid formation: The level of amyloid formation was detected using the above described Thioflavin T (ThT) dye binding assay. Fluorescence (relative intensity, measured in units of percent) of the ThT bound Aβ 1-42 remaining following 24 hours at 37° C., in the absence, and in the presence of 50 μM indole or indole derivative, was measured. Each measurement was recorded immediately after the fluorescence intensity reached a maximum value. The results obtained with representative indole derivatives, each representing a mean of four independent measurements along with an associated error bar representing a standard error, are graphically presented in FIG. 4.

Figure 4:
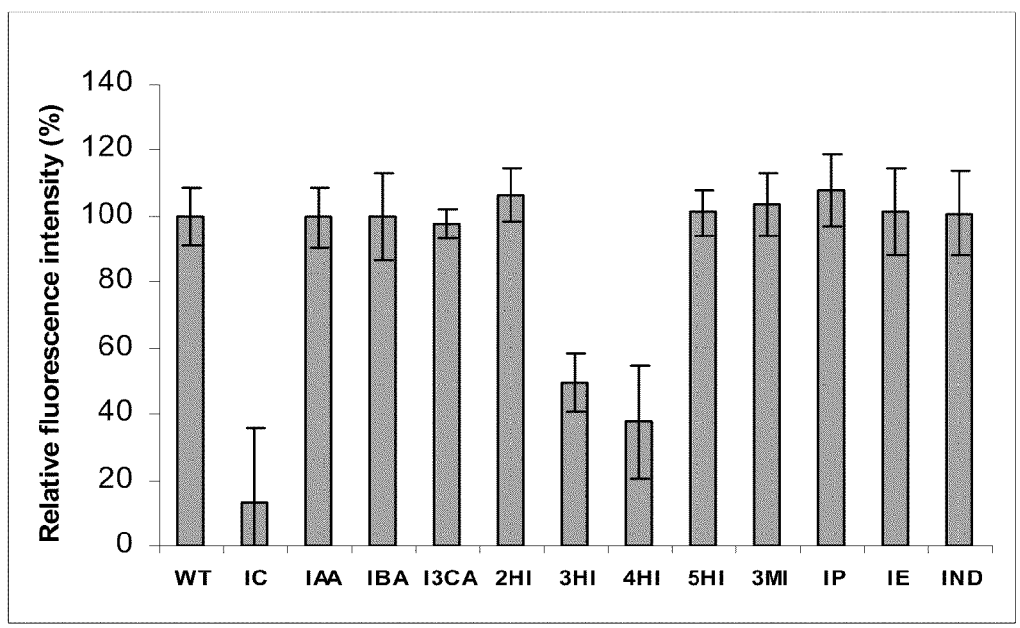
FIG. 4 presents a comparative bar graph illustrating the inhibition of β-amyloid fibril formation as effected by indole-3-carbinol (denoted as IC), 3-hydroxyindole (denoted as 3HI), and 4-hydroxyindole (denoted as 4HI), indole-3-acetic acid (denoted as IAA), indole-3-butyric acid (denoted as IBA), indole-3-carboxylic acid (denoted as I3CA), 2-hydroxyindole (denoted as 2HI), 5-hydroxyindole (denoted as 5HI), 3-methyl indole (denoted as 3MI), indole-3-propionic acid (denoted as IP), indole-3-ethanol (1E) and (denoted as IE)], unmodified indole (denoted as IND), and the control [(denoted as WT)—absent of any indole species], individually, as observed by monitoring fluorescence measurements during a Thioflavin T (ThT) fluorescence binding assay of Aβ 1-42 samples, in accordance with the present embodiments.

As is shown in FIG. 4, indole-3-carbinol (denoted as IC), 3-hydroxyindole (denoted as 3HI), and 4-hydroxyindole (denoted as 4HI), individually, significantly inhibited β-amyloid polypeptide fibril formation.

These results indicate that an effective inhibition of amyloid formation is particularly observed with indole derivatives that include one or more hydroxy groups. In each case of effective inhibition of amyloid formation, the indole derivative has a hydroxy (—OH) group, either directly (3-hydroxyindole, 4-hydroxyindole), or via a carbon linker (indole-3-carbinol), attached to the indole ring. Indole derivatives having, for example, a carboxylic acid or an alkyl attached directly or indirectly to the indole ring, did not exhibit an effective inhibition of amyloid formation.

Moreover, it appears that the inhibition functionality of the indole derivatives is further affected by the exact position of the —OH group, since, for example, 2-hydroxyindole (denoted as 2HI) or 5-hydroxyindole (denoted as 5HI) showed a significantly reduced inhibition of amyloid formation, as compared with indole-3-carbinol (denoted as IC), 3-hydroxyindole (denoted as 3HI), and 4-hydroxyindole (denoted as 4HI).

These results therefore further support the concept according to which the inhibition of amyloid formation is effected by aromatic interactions (induced by the indole skeleton) and is presumably further affected by hydrogen bonds, induced by the hydroxy group(s). These results further indicate that the distance between the aromatic moiety and the hydroxy group affects the inhibition activity, as demonstrated by the differential activity between 3HI, IC, and IE.

Concentration Dependence of Indole Derivatives inhibition activity: To examine the inhibition efficiency of the indole derivatives, the concentration dependence of inhibition of fibril formation was studied. The fibrillization of Aβ1-42, with and without an indole derivative was measured using the ThT fluorescence assay described above at a fixed incubation time of 24 hours. The results are presented in FIG. 5.

Figure 5:
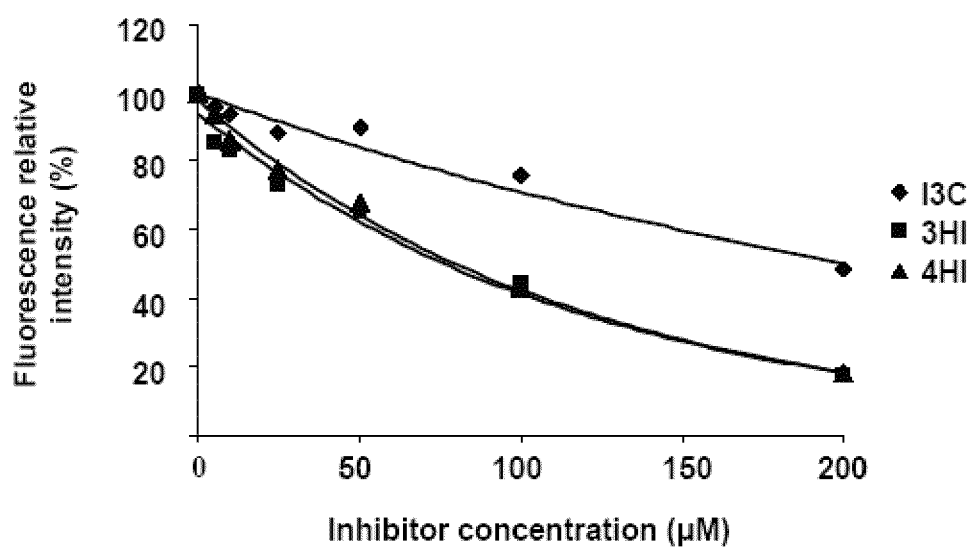
FIG. 5 presents comparative plots illustrating the inhibition of β-amyloid fibril formation as effected by various concentrations indole-3-carbinol (denoted as I3C, rhombus), 3-hydroxyindole (denoted as 3HI, squares), and 4-hydroxyindole (denoted as 4HI, triangles), individually, as observed by monitoring fluorescence measurements during a Thioflavin T (ThT) fluorescence binding assay of Aβ 1-42 samples, in accordance with the present embodiments.

As shown in FIG. 5, the 3-hydroxyindole (denoted as 3HI), and 4-hydroxyindole (denoted as 4HI) clearly showed a dose-dependent inhibition pattern. The indole-3-carbinol (denoted herein as I3C) inhibited the fibrillization of Aβ1-42 only at high concentrations and showed no dose-dependency.

The $IC_{50}$ values of each compound was calculated by the curve equation. The following apparent $IC_{50}$ values were obtained: about 85 μM for 4-hydroxyindole; about 100 μM for 3-hydroxyindole, and about 200 μM for indole-3-carbinol.

In order to rule out the possibility that the low values obtained in the ThT fluorescence assay may result from a quenching effect by the indole derivative a control experiment was conducted as follows: different concentrations of the three indole derivatives were added to form Aβ1-42 fibrils and fluorescence was immediately measured. No significant quenching effect was observed (data not shown).

Kinetics Studies of Aβ1-40 Fibrillogenesis Inhibition: Aβ1-40, which has a slower fibrillogenesis rate [see, Jarrett et al. (1993) *Biochemistry* 32, 4693-4697] was used in these studies, in order to obtain better temporal resolution, assuming that a slower rate would allow more significant inhibition and a better understanding of the effect. 3-Hydroxyindole (denoted as 3HI), 4-hydroxyindole (denoted as 4HI) and indole-3-carbinol (denoted herein as I3C) were each added at concentrations of 5 μM, 25 μM, and 50 μM to a solution containing 5 μM of Aβ1-40 (prepared as described above) and the kinetics of Aβ1-40 fibrillogenesis inhibition was measured using the ThT fluorescence assay.

Figure 6:
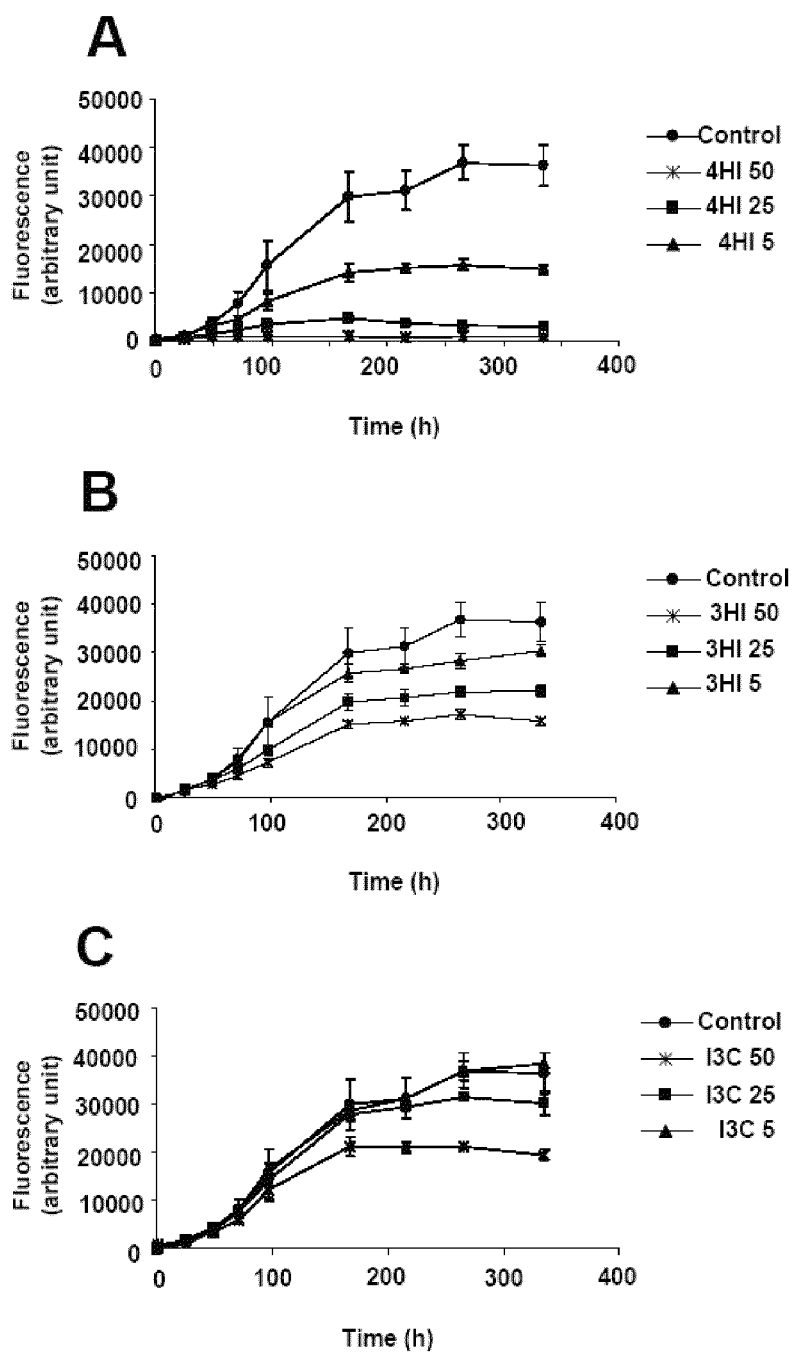
FIGS. 6a-c present comparative plots illustrating the kinetics of β-amyloid fibril formation following 14 days incubation of a fixed 5 μM concentration of Aβ1-40 with 5 μM (triangles), 25 μM (squares) and 50 μM (stars) of 4-hydroxyindole (denoted as 4HI, FIG. 6a), 3-hydroxyindole (denoted as 3HI, FIG. 6b), and indole-3-carbinol (denoted as I3C, FIG. 6c), or without an indole derivative (control, triangles), as observed by monitoring fluorescence measurements during a Thioflavin T (ThT) fluorescence binding assay of Aβ 1-40 samples, in accordance with the present embodiments.

The results obtained with 4-hydroxyindole are presented in FIG. 6a. The results obtained with 3-hydroxyindole are presented in FIG. 6b. The results obtained with indole-3-carbinol are presented in FIG. 6c. As is shown in FIGS. 6a-6c the ThT fluorescence curve obtained for all the tested indole derivatives showed a characteristic sigmoid shape representing three phases: the nucleation phase (lag phase), the polymerization phase, and the equilibrium phase (stationary phase).

As shown in FIG. 6a, samples containing 25 μM and 50 μM 4-hydroxyindole showed a significantly longer nucleation phase, which persisted throughout the duration of the measurements. In the sample containing 5 μM of 4-hydroxyindole, the effect on the nucleation phase was less significant.

As shown in FIGS. 6b and 6c, the samples containing 3-hydroxyindole and indole-3-carbinol, respectively, had no effect on the nucleation phase when compared with the control.

As is further shown in FIGS. 6a-6c, all the tested indole derivatives were inhibitory in the polymerization phase, such that with all the tested compounds the slope of the curve was changed, although with different magnitudes. Thus, I3C had an effect on the slope of the growth curve only at 50 μM whereby no effect was observed at lower concentrations (FIG. 6c). 3HI showed a dose-dependent effect, in which the slope of the growth curve changed in parallel with increasing concentrations of 3HI (FIG. 6b). The slope of the samples containing 5 μM 4HI was the most sharp, as compared with that of the control or the other tested indole derivatives.

Differences in the level of ThT fluorescence at the equilibrium phase are influenced by the ability of the indole derivative to redirect the Aβ away from the polymerization pathway. As shown in FIGS. 6a-6c, at the final equilibrium phase (at the endpoint of the experiments), 4HI exhibited the highest inhibition level at all the tested concentrations. The inhibition level of 4HI at 5 μM was almost 60%, whereby at 25 μM and 50 μM the inhibition level was almost complete (FIG. 6a). The inhibition level of 3HI at 25 μM was about 40%, and was about 60% at 50 μM (FIG. 6b). The inhibition level of I3C at 50 μM I3C was about 50% (FIG. 6c).

While recent evidence has indicated that the toxicity of Aβ and other amyloidogenic proteins lie in the soluble oligomeric forms [see, for example, Lambert et al. (1998) *Proc. Natl. Acad. Sci. U.S.A.* 95, 6448-6453; Wang et al. (2002) *Brain Res.* 924, 133-140; Walsh et al. (2002) *Biochem. Soc. Trans.* 30, 552-557; Kim, et al. (2003) *FASEB J.* 17, 118-120; Kayed et al. (2003) *Science* 300, 486-489; and Cleary et al. (2004) *Nature Neurosci.* 8, 79-84], notion has been made to the potential effect of anti-amyloid compounds in blocking Aβ oligomerization at a very early stage, most likely the neurotoxic stage.

The kinetic studies described herein are essential for determining the phases inhibited by each indole derivative and indeed have shown the ThT fluorescence assay is consistent with the nucleation-dependent polymerization model [Jarrett and Lansbury, (1993) *Cell* 73, 1055-1058; and Naikiet al. (1997) *Biochemistry* 36, 6243-6250]. The results obtained in these studies have showed that the indole derivative changes the shape of the fibrillogenesis curve in three ways: (i) interference with nucleation, leading to increase of the lag time; (ii) interference during the polymerization step, which significantly slows down the polymerization rate; and (iii) inhibition in which Aβ is diverted from the polymerization pathway, reducing the endpoint equilibrium level.

The results in these assays show that I3C and 3HI interfere in the polymerization stage and divert the process away from that pathway. 4HI seemed to interfere in all three steps.

Ultrastructural Analysis of amyloid fibril formation: The effect of the indole derivatives on the ultrastructural properties of the assembled Aβ was first evaluated by TEM measurements. Thus, TEM analysis was performed with samples of Aβ1-40 obtained from the kinetic studies described above after incubation for 14 days.

Figure 7:
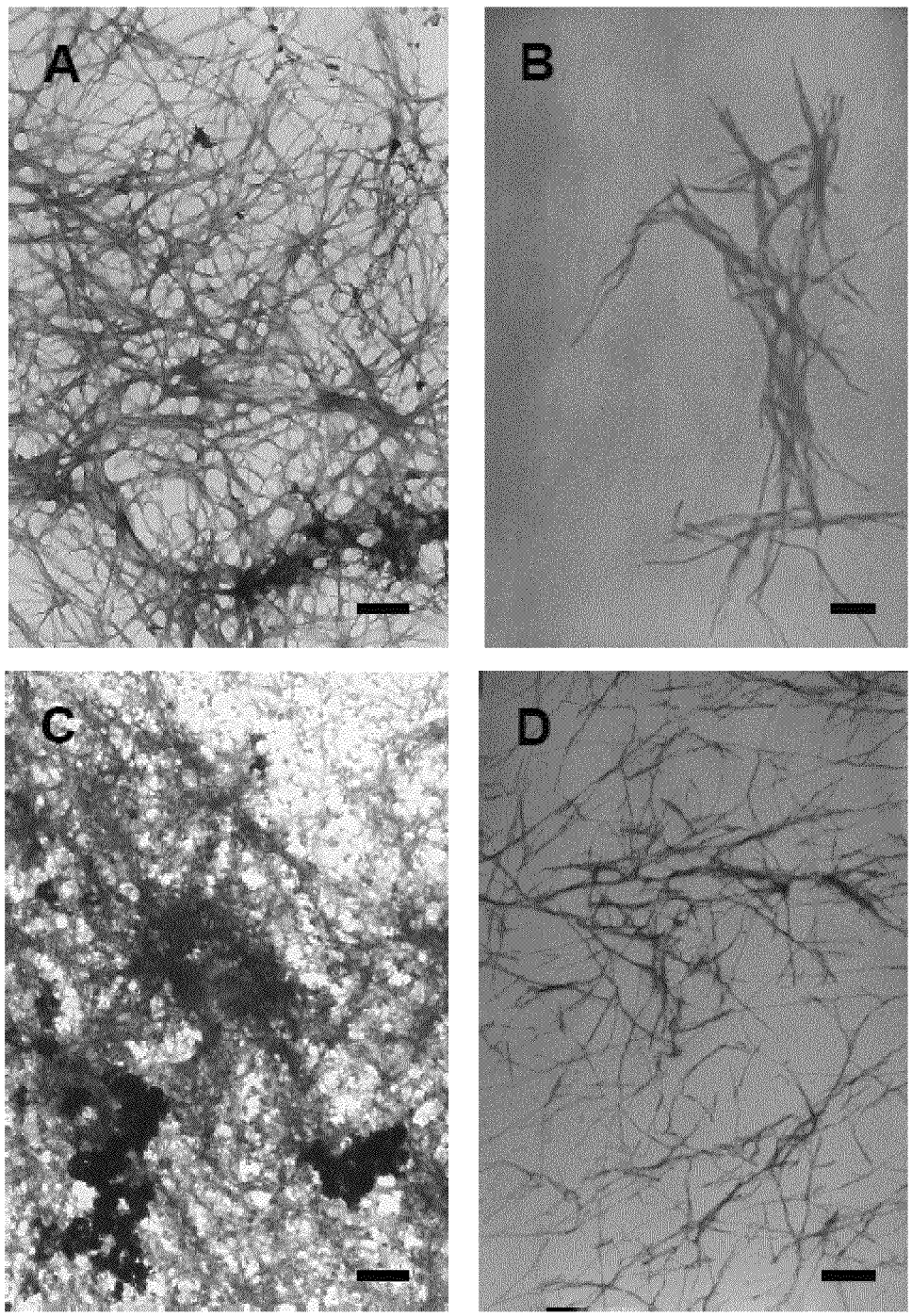
FIGS. 7a-d present electron micrographs (scale bar represents 200 nm) showing microstructural features of representative fluorescence assay samples of Aβ 1-40 (incubated for 14 days, per FIG. 5) in the absence (FIG. 7a) and presence of 25 μM 4-hydroxyindole (FIG. 7b), 50 μM 3-hydroxyincole (FIG. 7c), and 50 μM indole-3-carbinol (FIG. 7d)

The obtained micrographs of Aβ1-40 are presented in FIG. 7a (control), FIG. 7b (following 14 days incubation in the presence of 25 μM 4-hydroxyindole), FIG. 7c (following 14 days incubation in the presence of 50 μM) and FIG. 7d (following 14 days incubation in the presence of 50 μM indole-3-carbonil). As shown in FIG. 7a, control samples of Aβ1-40 contained abundant amyloid fibrils aggregated in PBS. As shown in FIG. 7c, samples containing Aβ1-40 and 25 μM 4HI were devoid of fibrils and contained only a minor amount of small fibrils. As shown in FIG. 7c, samples containing Aβ1-40 and 50 μM 3HI had a significant number of amorphous aggregates showing a congested form. It is assumed that the latter may affect the ThT measurements as a result of binding. As shown in FIG. 7d, samples containing Aβ1-40 and 50 μM I3C resulted in the same form as that observed in the control sample, although smaller amounts of amyloid fibril aggregates were observed.

These results stand in correlation with the above described quantitative fluorescence assays, and indicate that the only grids showing no amyloid fibrils were those containing samples of Aβ and 5 μM or more of 4HI.

Additional structural analyses were performed using AFM measurements, performed with Aβ1-40 samples taken from the kinetic studies once the control samples reached the different fibrillogenesis phase. None of the analyzed samples immediately showed amyloid fibrils (data not shown).

Figure 8:
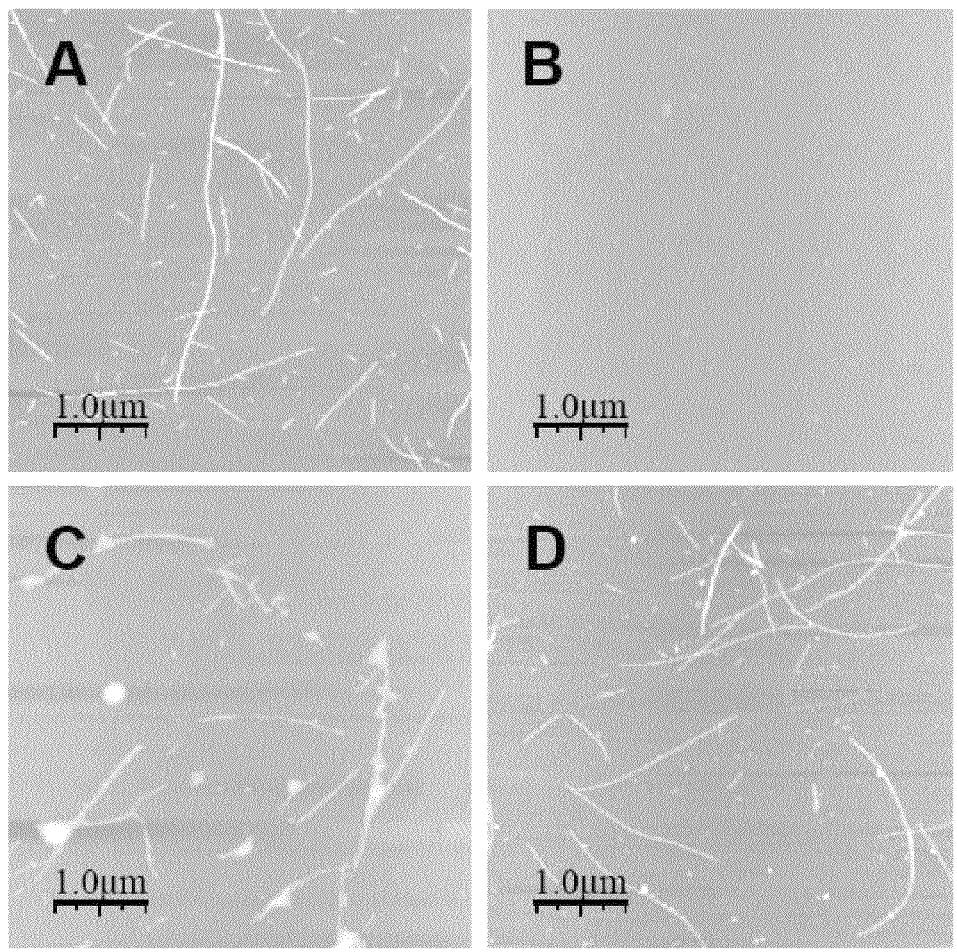
FIGS. 8a-d present AFM height images (5 μm×5 μm) showing structural features of representative fluorescence assay samples of Aβ 1-40 (per FIG. 5, taken once the control samples reached the polymerization phase), deposited on mica following incubation in the absence (control, FIG. 8a) and presence of 50 μM 4-hydroxyindole (FIG. 8b), 50 μM 3-hydroxyindole (FIG. 8c), and 50 μM indole-3-carbinol (FIG. 9d)

AFM measurements performed with Aβ1-40 samples taken from the kinetic studies once the control samples reached the polymerization phase showed different levels of amyloid fibril formation, as shown in FIGS. 8a-d. Thus, small amounts of amyloid fibrils in the form of long wires were observed in the control sample (FIG. 8a) and in the sample containing I3C (FIG. 8d), whereas samples containing Aβ1-40 and 4HI showed no fibrils (FIG. 8b). In samples containing 3HI a different fibril morphology was observed. As shown in FIG. 8c, in these samples small aggregates that interacted with the amyloid fibrils were observed.

These results therefore indicate that all the tested AFM samples were clear of fibrils in the immediate lag phase, and only those containing 4HI remained clear of amyloid fibrils in the following polymerization phase. These results support those of the kinetic assay in which the 4HI lag time was longer than in other samples and may suggest that 4HI blocks Aβ fibrillogenesis in the early stages of nucleation.

An apparent paradox was shown in the results obtained with 3-hydroxyindole. While a significant decrease occurred in the Aβ fibrillogenesis kinetic assay, this compound had no anti-cyclotoxic effect when tested with cultured PC12 cells, as discussed in detail hereinbelow. Without being bound to any particular theory, it is assumed that the variant morphology among the amorphous aggregates shown in the TEM micrograph (FIG. 7c) may be the reason for such a discrepancy.

Example 3

Materials and Experimental Methods

Cell culture: PC12 pheochromocytoma cell line, a cultured benign tumor of the sympathetic nervous system, was routinely grown in Dulbecco's Modified Eagle Medium (DMEM) supplemented with 8% (v/v) fetal calf serum, 8% (v/v) horse serum, 100 U/ml penicillin, 100 U/ml streptomycin, and 2 mM L-glutamine (Biological industries, Israel). The cells were maintained at 37° C. in a humidified atmosphere containing 5% $CO_2$.

Cell cytotoxicity assay: PC-12 cells ($3 \times 10^5$ cells/ml) were cultured in 96-well microplates (100 μl/well) and were incubated overnight at 37° C. The wells were then washed once with serum free-DMEM, so as to exclude the effect of the serum. To each well 100 μl of 5 μM Aβ1-40 (prepared from a stock solution of 0.5 mM in 10 mM NaOH) and an indole derivative at various concentrations were added. Each determination was made in quadruplicate. Following incubation for 24 hours at 37° C., cell viability was evaluated using the MTT assay (as described in Hansen et al. (1989) *J. Immunol. Methods* 119, 203-210).

EXPERIMENTAL RESULTS

The effect of the indole derivatives on the formation of cytotoxic amyloid assemblies was determined by measuring the toxicity of the formed Aβ on pheochromocytoma cell line cultures (PC12) in the presence and absence of the indole derivatives. Thus, solutions of 5 μM Aβ1-40 and various concentrations of the indole derivatives 3HI, 4HI and I3C were prepared and added to the cells at two time points: immediately (T=0) or 7 days after incubation. Cell viability was determined after 24 hours using the MTT assay. Cells incubated with only 5 μM Aβ1-40 served as the control.

Figure 9:
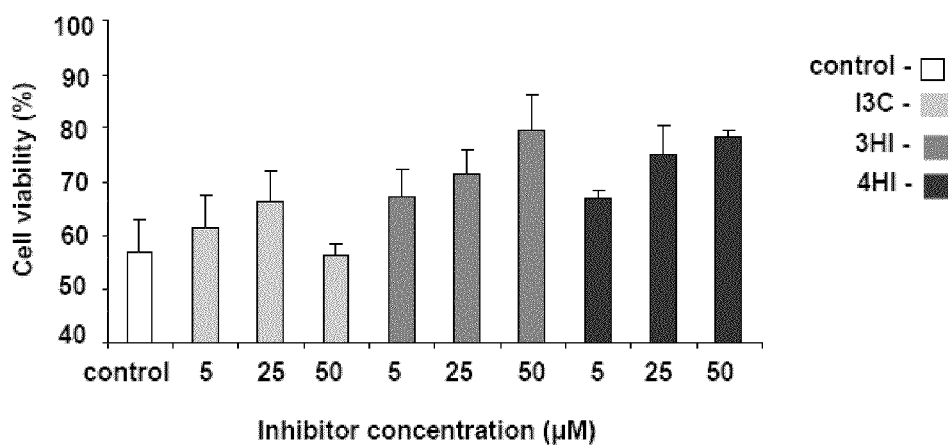
FIGS. 9a-b present bar graphs demonstrating the effect of a solution containing Aβ 1-40 in the absence (control) and presence of various concentrations of indole-3-carbinol (denoted I3C), 3-hydroxyindole (denoted 3HI) and 4-hydroxyindole (denoted 4-HI), immediately following its preparation (FIG. 9a) and following 7 days incubation (FIG. 9b) on the viability of PC12 cells.
Figure 9:
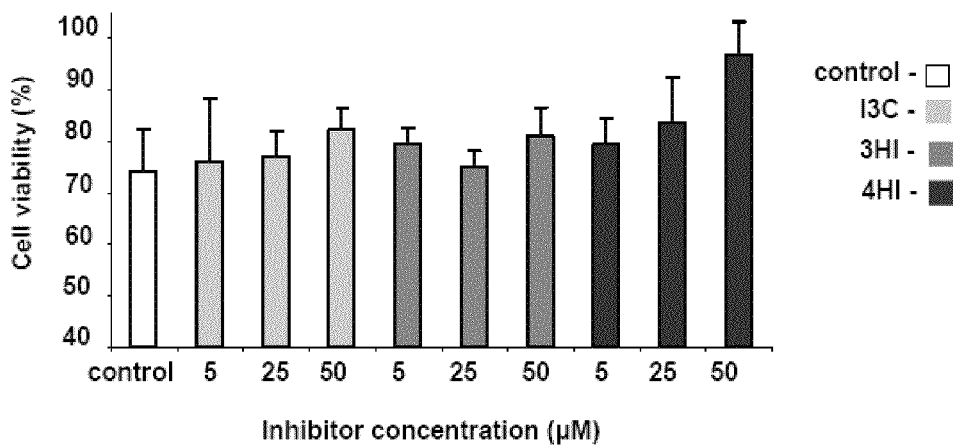

The results obtained following addition of the above solutions immediately after their preparation (T=0) represent the cytotoxic effect during the first 24 hours of Aβ fibrillogenesis and are presented in FIG. 9a. The results obtained following addition of the above solutions after 7 days incubation (T=7) represent the cytotoxic effect at the end point phase, when large and congested amyloid fibrils were already formed, and are presented in FIG. 9b.

As shown in FIG. 9a, the average survival rate at T=0 with various concentrations of the various indole derivatives, was about 56%. As shown in FIG. 9b, at T=7, the survival rate of the control was about 74%. This survival rate was higher than that at T=0.

As is further shown in FIGS. 9a-b, 4HI had the most significant inhibitory effect on Aβ1-40 cytotoxicity in both cell culture assays. Thus, for example, upon addition of solutions containing Aβ1-40 and 25 or 50 μM of 4HI, the viability rate of PC12 cells was elevated by about 25% as compared with the control. Addition of solutions containing 3HI, improved the PC12 survival rate by about 25% as compared with the control only at T=0. No significant inhibition of cytotoxicity was observed with I3C in either assay.

When solutions containing only the indole derivatives were added to the cells, no effect on the survival of PC12 cells was observed (data not shown).

Figure 10:
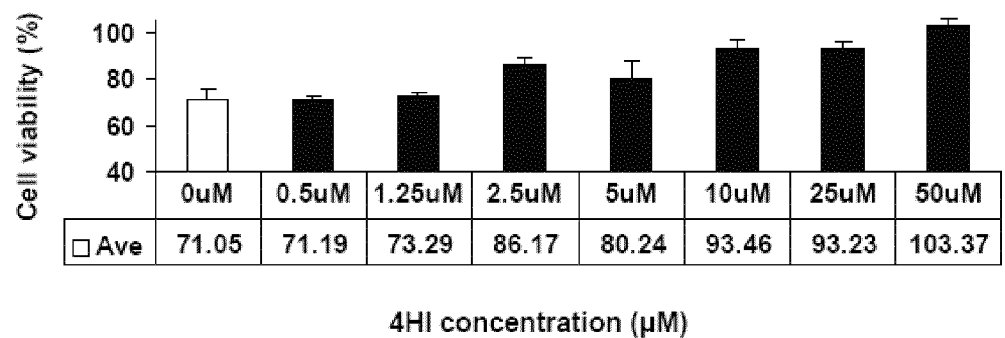
FIG. 10 presents a bar graph showing the effect of a solution containing Aβ 1-40 in the absence (control) and presence of various concentrations of 4-hydroxyindole (denoted 4-HI), following 7 days incubation (FIG. 9b), on the viability of PC12 cells.

The protective effect of 4HI was further defined by adding solutions containing 5 μM Aβ1-40 and various concentrations of 4HI, ranging from 0.5 μM to 50 μM, to PC-12 cells, following 7 days incubation of the solution. The results are presented In FIG. 10 and clearly show that the protective effect of 4HI is dose-dependent. The obtained results further indicate that the minimum concentration of 4HI required for significant inhibition was 2.5 μM, whereas the toxic effect of Aβ1-40 was completely blocked at 50 μM 4HI.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of treating Alzheimer's disease in a subject in need thereof, the method comprising administering to the subject a therapeutically effective amount of indole-3-carbinol.

* * * * *